United States Patent
Unger et al.

(10) Patent No.: US 6,268,340 B1
(45) Date of Patent: Jul. 31, 2001

(54) IN VIVO REGENERATION OF OLIGODENDROCYTES BY BOLUS INJECTION OF NGFβ

(75) Inventors: Jürgen Unger, Landshut; Ilse Bartke, Bernried; Kurt Naujoks, Penzberg; Yorn Schmidt, München, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/894,709

(22) PCT Filed: Mar. 8, 1996

(86) PCT No.: PCT/EP96/00992

§ 371 Date: Sep. 8, 1997

§ 102(e) Date: Sep. 8, 1997

(87) PCT Pub. No.: WO96/28180

PCT Pub. Date: Sep. 19, 1996

(30) Foreign Application Priority Data

Mar. 10, 1995 (DE) .................................. 95103458

(51) Int. Cl.⁷ .................................. A61K 38/18
(52) U.S. Cl. .................................. 514/12; 514/2
(58) Field of Search ........................... 514/2, 12

(56) References Cited

U.S. PATENT DOCUMENTS 5,885,584 * 3/1999 Althaus et al. .

FOREIGN PATENT DOCUMENTS

93/03140   2/1993   (WO) .

OTHER PUBLICATIONS

Unger et al., Poster presented at the *Annual Meeting of the Society for Neuroscience*, San Diego, California, Nov. 11–16, 1995, "Time course of regeneration in the adult pig brain following lysolecithin–induced demyelination".

Althaus et al., *Neurosci. Lett.* 135 (2) (1992) pp. 219–223, "Nerve growth factor induces proliferation and enhances fiber regeneration in oligodendrocytes isolated from adult pig brain".

Olson et al., *Arch Neurol.* 48 (4) (1991) pp. 373–387, "Intraputaminal infusion of nerve growth factor to support adrenal medullary autografts in Parkinson's disease one–year follow–up of first clinical trial".

Olson et al., *J. Neural. Transm. Parkinson's Dis. Dementia Sect.* 4 (1) (1992) pp. 79–96, "Nerve growth factor affects carbon–11 nicotine blinding blood flow eeg and verbal episodic memory in an Alzheimer patient".

Engel et al. (1994) NeuroReports, 5(4), "NGF Increases $[Ca^{2+}]_i$ in Regenerating Oligodendroglial Cells", pp. 397–400.*

* cited by examiner

Primary Examiner—Jon P. Weber
(74) Attorney, Agent, or Firm—Arent Fox Kintner Plotkin & Kahn PLLC

(57) ABSTRACT

A method is presented for regenerating oligodendrocytes in diseases such as multiple sclerosis by administering human β nerve growth factor (NGF-β) by bolus injection. Treatment comprises 1–10 bolus injections in a dose of 0.05 to 5.0 μg/kg body at an interval of 1 to 21 days.

11 Claims, 1 Drawing Sheet

IN VIVO REGENERATION OF OLIGODENDROCYTES BY BOLUS INJECTION OF NGFβ

Figure 1:
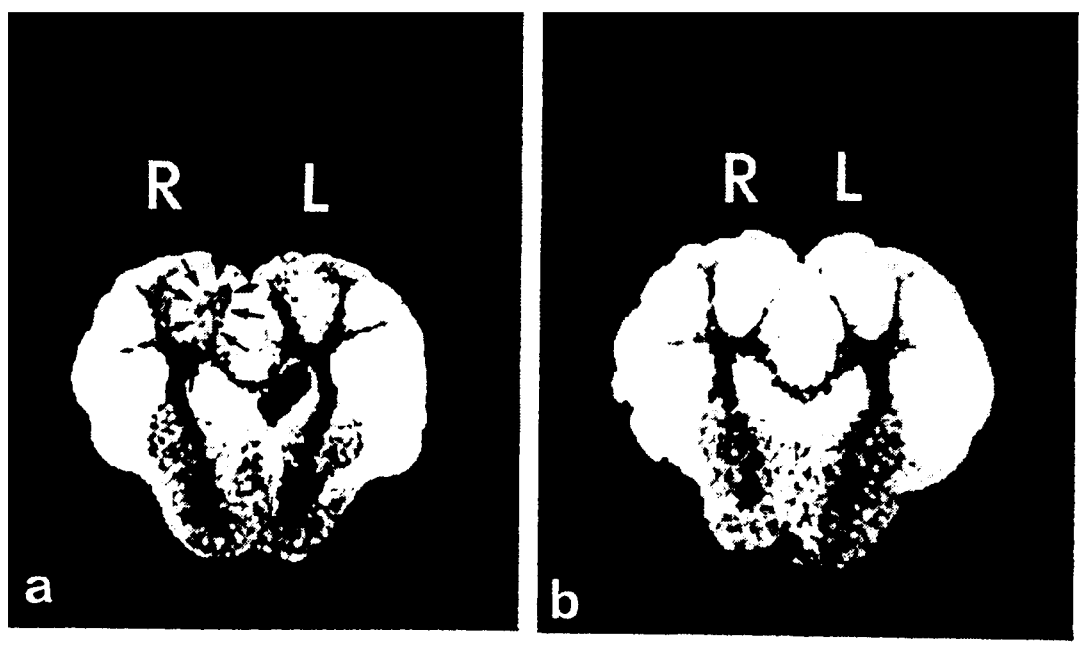

The present invention concerns a novel method for the regeneration of oligodendrocytes, in particular, of human oligodendrocytes, and for the treatment of diseases in which a demyelination of nerve fibers occurs, a method of manufacturing a therapeutic agent, as well as the use of human β nerve growth factor (NGF) for said therapeutic use.

The covering of nerve fibers in the central nervous system (CNS) with myelin is essential for the function of neuronal signal transmission. The myelin sheath is formed by oligodendrocytes (OL), the fibers of which wrap around the axon of a nerve cell. Demyelinating diseases such as multiple sclerosis in which the myelin sheath of the axon is damaged or destroyed also lead to impairments of the OL. However, the OL remains capable of regenerating the myelin sheaths. Therefore, the identification and characterization of factors which are responsible for increased regeneration of OL is very important for the molecular understanding of demyelination diseases, such as multiple sclerosis (MS), and for the development of therapeutic agents.

It is known from PCT/EP92/01173 (17) that the regeneration of oligodendrocytes is improved when they are treated with NGF or active fragments of NGF.

NGF is a neurotrophic factor which is well characterized. Its gene is described in Ullrich et al. (1993) (1) and EP-B 0 121 338 (U.S. Pat. No. 5,169,762) (13). The recombinant production of NGF from *E.coli* is described in EP-A 0 544 293 (15), EP-A 0 450 386 (U.S. Pat. No. 5,235,043) (14), EP-A 0 370 171 (16) and U.S. Ser. No. 08/266610 (18).

NGF has potent and beneficial effects on cholinergic neurons after axotomy (see, for example, Hoffman et al. (1990) (2)). NGF infusions stimulate the regeneration of transsected cholinergic neurons (Gage (1988) (3), Tuszynski et al. (1990) (4)). It is further known that infusions of NGF stimulate the expression of choline acetyltransferase (ChAT) (Hefti et al. (1984) (5) and p75NGF receptor mRNA (Gage et al. (1989) (6)).

For the therapeutic application, NGF is infused for a period of several weeks. Olson et al. (1991) (11) describes an infusion of NGF through an intraventricular cannula for 23 days with a total dose of 3.3 mg (corresponding to approximately 140 µg/24 hr) for the treatment of Parkinson's patients after having received fetal dopaminergic grafts. It is also known to deliver NGF therapeutically in Alzheimer's disease via a programmable pump planted subcutaneously into the abdominal wall and connected by a subcutaneous catheter to the intraventricular catheter. To the patient a total of 6.6 mg of NGF was delivered during three months at a rate of 15 µl/hr (corresponding to approximately 75 µg/24 hr (Olson et al. (1992) (12))).

SUMMARY OF THE INVENTION

It was surprisingly found that for the regeneration of oligodendrocytes, i.e. in MS, an interval application leads to an improved and accelerated remyelination of damaged nerve fibers as compared to continuous application of the therapeutic agent.

The invention concerns a method of preparing a therapeutic agent for the treatment of multiple sclerosis, the method being characterized in that human β nerve growth factor (NGF) is brought into a pharmaceutically acceptable formulation for administering in a dose between 0.05 µg and 5 µg/kg body weight in 1 to 10 bolus injections at an interval of 1 to 21 days, preferably 1 to 12 days.

According to the invention, NGF is administered in a dose between 0.05 µg and 5 µg/kg, 3.5 to 350 µg, preferably 3.5 to 210 µg per injection, at an interval of 1 to 21 days. Preferably, the dose is applied in 1 to 10 injections.

In a preferred embodiment of the invention, it is preferred to use 0.01 µg to 3 µg/kg, and more preferably 0.1 µg to 1 µg/kg.

It is preferred to administer NGF intrathecally, into the cerebrospinal fluid space of the ventricle or spinal cord, preferably of the lateral ventricle or the lumbar spinal cord.

DETAILED DESCRIPTION OF THE INVENTION

The term "NGF" means β-unit of human NGF. β-NGF has an amino acid sequence of 118 amino acids and is present as a dimer in solution. The amino acid and DNA sequence is described in Ullrich et al. (1993) (1).

The pharmaceutical compositions which are used according to the invention and contain β-NGF may be administered in any sterile biocompatible pharmaceutical carrier, including, but not limited to, saline, buffered saline or dextrose solution, preferably in an acidic solution having a pH of about 4 to 5, preferably in an acetate buffer. The amount of NGF protein which will be effective in the treatment of MS is in a dose between 0.05 µg and 5 µg/kg body weight at an interval of 1 to 21 days, preferably in 1 to 10 injections. It is further preferred to use 3.5 to 350 µg/injection.

Methods of introduction include, but are not limited to, intradermal, intramuscular, intraperitoneal, intravenous, subcutaneous, oral, intrapeulmonal and intranasal administration. In addition, it may be desirable to introduce the pharmaceutical composition of the invention into the central nervous system by any suitable route, including intrathecal, e.g. intraventricular injection. Intraventricular injection may be facilitated by an intraventricular catheter, for example attached to a reservoir, such as an implantable port catheter system, such as the Periplant® filtrosafe (B. Braun GmbH, Spangenberg, DE).

Furthermore, it may be desirable to administer the pharmaceutical compositions, which are used according to the invention, locally to the area in need of treatment. This may be achieved by, for example, and not by way of limitation, injection by means of a catheter or by means of an implant, said implant being of a porous, non-porous or gelatinous material, including membranes, such as sialastic membranes or fibers. NGF is preferably administered during the relapse period. If high doses are used, only a few or even one bolus application is sufficient.

The following examples and FIG. 1 are provided to aid the understanding of the present invention, the true scope of which is set forth in the appended claims. It is understood that modifications can be made in the procedures set forth without departing from the spirit of the invention.

FIG. 1 shows coronal magnetic resonance tomography imaging (MRI) of pig brains 7 days after lysolecithin-induced demyelination. a) Lesioned animal, receiving sham-treatment with a single intraventricular injection of 70 µg Cytochrom C. Arrows point to hyperintensity in the subcortical white matter of the lesioned side (R—right hemisphere) as compared to the non-lesioned left hemisphere (L). b) Identically lesioned animal as shown in a), receiving a single intraventricular injection of 70 µg NGF. Note that both hemispheres are symmetrically configured with no remaining hyperintensity in the lesioned side (R).

EXAMPLE 1

Experimental Design of an Animal Model of Demyelination

Lesion

An experimental model of demyelination was established in the female, adult "Göttingen Mini Pig" (age: 10–14 months, weight: 25–30 kg) by stereotaxic injection of lysolecithin (LL) at multiple sites into the periventricular subcortical white matter of the brain (usually 2–3 injection sites located in one hemisphere; 5 to 25 $\mu$l of 1% LL in 0.9% saline per lesion infused over a period of 15 min). This infusion causes a rapid reduction of myelin sheaths within the diffusion area of the detergent (Blakemore (1978) (7)).

NGF-application

Immediately after LL application, a catheter system (Periplant Filtrosafe®, Braun, Melsungen, Germany) is implanted either into the lateral ventricle of the brain or in the subarachnoidal space of the lumbar spinal cord (Motsch and Robert (1987) (8); Krames and Lanning (1993) (9)). Two ways of NGF application were used:

1) After fixation of the catheter with Ionocem® bone cement (Ionos, Seefeld, Germany) the intrathecal catheter is connected with a subcutaneous drug delivery system (Periplant Filtrosafe®, Braun, Melsungen, Germany) which is implanted subcutaneously in the upper back region. NGF (dissolved in phosphate-buffered saline, pH 7.2) injected every 2nd day through the skin into the port, starting 1 day after initial LL lesions, by single bolus injections into the port at a dose of 0.05–3 $\mu$g/kg body weight (1.25 to 90 $\mu$g per injection, corresponds to 3.5 to 210 $\mu$g per injection (human weight: 70 kg). 1–5 injections were carried out into the cerebrospinal fluid within a period of 1–12 days after LL-induced demyelination.

2) The effect of single bolus injections of NGF described above was compared with the continuous infusion of NGF into the lateral ventricle via osmotic minipumps (Alzet® for 1–12 days at a dose of 0.5 $\mu$g/h).

Controls

Controls were carried out by replacement of NGF solution with an equal dose of Cytochrome C applied in the same ways and time interval as described in 1) and 2).

Evaluation of NGF effects

At the end of the NGF (control, respectively) application period, the experimental animals were sacrificed, the brain was removed and prepared for histological examination: The areas of interest were studied with routine histological (H.E. staining, Luxol Fast Blue staining), immunocytochemical (myelin basic protein—MBP) and electronmicroscopic (oligodendrocytes, myelin lamellae) procedures.

Findings

Injection of LL causes a widespread demyelination throughout the area of diffusion.

Chronic infusion of infusion of NGF via Alzet pumps: An improved and accelerated remyelination of the lesioned myelin sheaths of nerve fibers was detected within the application interval as compared to controls. Significant regeneration was observed 7 days after initial lesion whereas severe demyelination was still present in the white matter of sham-treated animals.

Bolus NGF injection every 2nd day: Significant regeneration was also noted under NGF treatment in this system, with no apparent differences to animals receiving chronic infusions of NGF. Furthermore, NGF injected in the CSF space in the area of the spinal cord showed the same positive effect on remyelination as found for intraventricular injections.

The data demonstrate that injections of NGF into the cerebrospinal fluid lead to an improved and accelerated remyelination, most likely due to regeneration and proliferation of oligodendrocytes. Compared to chronic NGF infusion with the help of pumps, the application via an intrathecally implanted port allows an easy-to-handle, save and inexpensive way of supplying the brain with the neurotrophin at an adjustable and optimal concentration for maximal therapeutic efficacy. In addition, in patients with multiple sclerosis suffering from repeated attacks (i.e. relapsing-remitting MS) immediate interval treatments at the time of the attack within a period of several years are possible, minimizing the risk of complications (i.e. infections) due to necessary changes of catheter systems or refills of pumps needed during chronic or repeated infusions.

Additional Supporting Data

There is a clear correlation between the degree of remyelination and functional improvements in the state of demyelinating diseases (IFNβ study group (1993) (10)).

Data obtained from animal models using pigs have a great clinical relevance in biomedical research, i.e. numerous studies on the cardiovascular system, skin and peripheral nervous system that have proven that data from porcine tissue are applicable on human subjects.

List of References (1) Ullrich et al., Nature 303 (1993) 821
(2) Hoffman et al., Exp. Neurol. 110 (1990) 39–44
(3) Gage, F. H., J. Comp. Neurol. 269 (1988) 147–155
(4) Tuszynski, M. H., et al., Neuroscience 36 (1990) 33–44
(5) Hefti, F., et al., Brain Res. 293 (1984) 305–311
(6) Gage, F. H., et al., Neuron 2 (1989) 1177–1184
(7) Blakemore, W. F., Neuropathol. Appl. Neurobiol. 4 (1978) 47–59
(8) Motsch, J., and Robert, B., Schmerz 3 (1987) 115–125
(9) Krames, E. S., Lanning, R. M., J. Pain Symptom Manage. 8 (1993) 539–548
(10) The IFNβ multiple sclerosis study group, Neurology 43 (1993) 662–667
(11) Olson, L., et al., Arch. Neurol. 48 (1991) 373–381
(12) Olson, L., et al., J. Neural. Transm. [P-D Sect] 4 (1992) 79–95
(13) EP-B 0 121 338 (U.S. Pat. No. 5,169,762)
(14) EP-A 0 450 386 (U.S. Pat. No. 5,235,043)
(15) EP-A 0 544 293
(16) EP-A 0 370 171
(17) PCT/EP92/01173
(18) U.S. Ser. No. 08/266,610

What is claimed is:

1. A method of regenerating oligodendrocytes for the treatment of a disease in a human in which a demyelination of nerve fibers occurs, comprising the steps of bringing human β nerve growth factor into a pharmaceutically acceptable formulation for administration to a human; and administering the human β nerve growth factor by bolus injection to the human, wherein each bolus injection is in an amount of the human β nerve growth factor of 0.05 $\mu$g to 5 $\mu$g/kg body weight of the human, and wherein the administration involves 1 to 10 bolus injections over a time interval of 1 to 21 days.

2. The method of claim 6, wherein each bolus injection has an amount of the human β nerve growth factor of 0.1 $\mu$g to 3 $\mu$g/kg body weight of the human.

3. The method of claim 1, wherein each bolus injection has an amount of the human β nerve growth factor of 0.1 $\mu$g to 1 $\mu$g/kg body weight of the human.

4. The method of claim 1, wherein the human β nerve growth factor is administered in a dose from 3.5 μg to 350 μg/bolus injection.

5. The method of claim 1, wherein the human β nerve growth factor is administered in a dose from 3.5 μg to 210 μg/bolus injection.

6. The method of claim 1, wherein the human β nerve growth factor is administered over a time interval of 1 to 12 days.

7. The method of claim 1, wherein the human β nerve growth factor is administered intrathecally into the cerebrospinal fluid space of the ventricle or spinal cord of the human.

8. The method of claim 7, wherein the human β nerve growth factor is administered into the lateral ventrical or the lumbar spinal cord.

9. The method according to claim 7, wherein the administration of the human β nerve growth factor into the cerebrospinal fluid is an intraventricular bolus injection carried out via an intraventricular catheter attached to an implanted port for injection.

10. The method of claim 6, wherein the human β nerve growth factor is administered intradermally, intramuscularly, intraperitoneally, intravenously, or subcutaneously.

11. The method of claim 6, wherein the human β nerve growth factor is administered by catheter to an area of the human in need of treatment.

* * * * *